(12) United States Patent
Andersson et al.

(10) Patent No.: US 8,137,549 B2
(45) Date of Patent: *Mar. 20, 2012

(54) AUTOMATED PACKING SYSTEM AND METHOD FOR CHROMATOGRAPHY COLUMNS

(75) Inventors: Torvald Andersson, Uppsala (SE); Mats Olsson, Uppsala (SE); Bengt Asberg, Uppsala (SE); Lars Andersson, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 916 days.

This patent is subject to a terminal disclaimer.

(21) Appl. No.: 12/173,906

(22) Filed: Jul. 16, 2008

(65) Prior Publication Data

US 2008/0272045 A1    Nov. 6, 2008

Related U.S. Application Data

(63) Continuation of application No. 11/179,925, filed on Jul. 12, 2005, now Pat. No. 7,419,599.

(51) Int. Cl.
*B01D 15/08* (2006.01)
(52) U.S. Cl. ............... 210/198.2; 210/656; 210/143
(58) Field of Classification Search ............ 210/635, 210/656, 143, 198.2, 232; 141/12, 73, 80
See application file for complete search history.

(56) References Cited

U.S. PATENT DOCUMENTS

| 4,350,595 | A | 9/1982 | Gunkel |
| 5,610,322 | A | 3/1997 | Unger et al. |
| 5,951,873 | A | 9/1999 | Shalon et al. |
| 6,001,260 | A | 12/1999 | Hatch et al. |
| 6,123,849 | A | 9/2000 | Purdom |
| 6,139,732 | A | 10/2000 | Pelletier |
| 7,132,053 | B2 | 11/2006 | Hauck et al. |
| 2003/0089662 | A1* | 5/2003 | Hofmann ............... 210/656 |
| 2004/0016701 | A1 | 1/2004 | Hauck et al. |
| 2006/0196832 | A1 | 9/2006 | Perreault et al. |
| 2006/0219616 | A1 | 10/2006 | Noyes et al. |
| 2007/0090053 | A1 | 4/2007 | Windahl |
| 2009/0038381 | A1* | 2/2009 | Windahl ............... 73/61.56 |

FOREIGN PATENT DOCUMENTS

WO    WO 02/10739    2/2002

OTHER PUBLICATIONS

Cherrak, D., et al., "Behavior of packing materials in axially compressed chromatographic columns" Journal of Chromatography A, 943 (2001) 15-31.

Hofmann, M., "Use of ultrasound to monitor the packing of large-scale columns, the monitoring of media compression and the passage of molecules, such as monoclonal antibodies, through the column bed during chromatography" Journal of Chromatography A, 989 (2003) 79-94.

Stanley, B., et al., "Consolidation of the packing material in chromatographic columns under dynamic axial compression IV. Mechanical properties of some packing materials" Journal of Chromatography A, 741 (1996) 175-184.

* cited by examiner

*Primary Examiner* — Ernest G Therkorn

(57) ABSTRACT

A column packing system comprises a control unit provided with software for calculating the breakpoint where a movable adapter comes into contact with a settled bed of bed media. The calculated breakpoint is used by the control unit to determine how much further the movable adapter has to move into the column in order to achieve a desired amount of bed compression.

4 Claims, 2 Drawing Sheets

US 8,137,549 B2

AUTOMATED PACKING SYSTEM AND METHOD FOR CHROMATOGRAPHY COLUMNS

CROSS-REFERENCE TO RELATED APPLICATIONS

This application is a continuation of U.S. patent application Ser. No. 11/179,925 filed Jul. 12, 2005, now U.S. Pat. No. 7,419,599; the disclosure of which is incorporated herein by reference in its entirety.

FIELD OF THE INVENTION

The present invention relates to a media packing system for columns and a media packing method for use in columns. More specifically, the invention relates to packing devices and methods for improving the packing of chromatography media into chromatography columns.

BACKGROUND OF THE INVENTION

Columns used in liquid chromatography typically comprise a tubular body enclosing a porous chromatography media through which a carrier liquid flows, with separation taking place by material collection between the carrier liquid and solid phase of the porous media. Typically, the porous media is enclosed in the column as a packed bed, typically formed by consolidating a suspension of discrete particles, known as slurry that is pumped or poured or sucked into the column, usually from one end. Consolidating of the slurry into a packed bed is achieved by compressing the slurry so that it is packed into a volume which is less than the volume that it would have occupied if it had sedimented under the influence of only gravity to form a sedimented bed. The efficiency of subsequent chromatographic separation relies strongly on the liquid distribution and collection system at the fluid inlet and outlet of the packed bed, and on the compression of the packed bed. If the compression of the compressed bed is too low then chromatographic separations performed on the bed suffer from "tailing". If the compression of the compressed bed is too high then chromatographic separations performed on the bed suffer from "leading". If the compression is optimum then the separation peaks formed during use exhibit neither leading nor tailing and are substantially symmetrical. The optimum degree of compression required for a column is determined experimentally for each column size (width or diameter), bed height and bed media.

Prior to any separation process, the bed has to be prepared starting from the slurry of particles that has to be introduced into the column. The process of bed formation is called 'the packing procedure' and a correctly packed bed is a critical factor influencing the performance of a column containing a packed bed. The goal of the packing procedure is to provide a bed compressed by the optimum amount of compression— the optimum compression factor. Large scale columns are preferably prepared by injecting into the column, through a central slurry nozzle, a predetermined volume of a slurry having a specified concentration of media particles. Once the predetermined volume of slurry has been injected into the column it may be compressed by moving a movable adapter down the longitudinal axis of the column towards the bottom of the column, normally at a constant speed, e.g. 1 cm per minute. The excess liquid during this procedure is removed at the column outlet, while the particles are retained by means of a filter material, a so-called 'bed support', with pores too small to allow the particles to pass though. The packing process is complete once the packed bed has been compressed by the optimum amount. The packing process is considered as being successful if the compressed bed allows for a good and robust chromatographic performance quantified in terms of the residence time distribution over the bed. However, producing such an optimally compressed bed is not easy to achieve in practice. Bed packing has hitherto been regarded as an art rather than a science and the quality of the final packed bed is dependant on the skill of the operator controlling the filling of the column. One reason for this is that it is difficult to ensure that the actual slurry concentration fed in the column is exactly the same as the specified concentration used in the calculation of how much slurry should be fed into the column. During filling and the subsequent packing of the column, the operator manually selects and adjusts the packing parameters such as flow rates, adapter speed of advancement and bed compression, and has to judge the point when the adapter starts compressing the bed. This point is used to calculate how much further the adapter must move in order to obtain the required amount of compression. Mistakes in the selection of any of these packing parameters may lead to a poorly performing column. It is particularly difficult to judge by eye when compression of the bed actually starts and a significant error at this point makes it impossible to obtain an optimally compressed bed.

As used herein and in the appended claims: the term "fluid system" is intended to designate the apparatus in which liquid is either introduced to or withdrawn from a cell at a zone approximately transverse the direction of flow through the cell. The term "cell" is intended to include the terms "vessel" and "column", as well as any other structure utilised by practitioners of the separation arts, to effect a separation, and/or reaction, and/or catalysation, and/or extraction of components from an admixture by bringing the admixture into contact with solid or liquid exchange media, known as the packed bed. "Cross-sectional zone" (or region or portion) refers to a region within a cell bounded by cross sections of the cell-oriented transverse (typically approximately normal) the longitudinal direction of flow through the cell. "Longitudinal direction of flow" refers to the direction of flow from an inlet towards an outlet within a cell. "Longitudinal" is used consistently to designate the dominant flow path of fluid through a cell without regard to direction. "Flow connection system" refers to a system of channels or paths that connect two points in a fluid circuit. "Distribution system" refers to structures through which fluids are introduced to a cell and "collection system" refers to structures used to collect fluids from a cell, in each instance from a cross-sectional zone.

"Sedimented bed height" refers to the height of a bed of bed media particles which is obtained when a bed of media particles is formed after a slurry of media particles is allowed to sediment under the influence of gravity only—such a bed is called a "sedimented bed". "Settled bed height" refers to the height of a bed of bed media particles that is obtained when a bed of media particles is formed after a slurry of media particles is forced to sediment under the influence of gravity and an additional downward force exerted on the bed particles, for example by the flow of fluid through the bed caused by the descent of a movable adapter towards the bed and/or liquid pumped through the bed—such a bed is called a "settled bed".

SUMMARY OF THE INVENTION

The object of the invention is to provide a column packing system and a method for packing media into columns which overcomes the drawbacks of the prior art systems. Embodiments of the invention are defined in the dependent claims.

Further improvements are mentioned in the dependent claims.

One advantage with devices and methods in accordance with the present invention is that they provide beds packed to an optimum compression factor. A further advantage of such devices and methods is that they permit the reproducible and controllable packing of chromatographic columns.

DETAILED DESCRIPTION OF THE INVENTION

Figure 1:
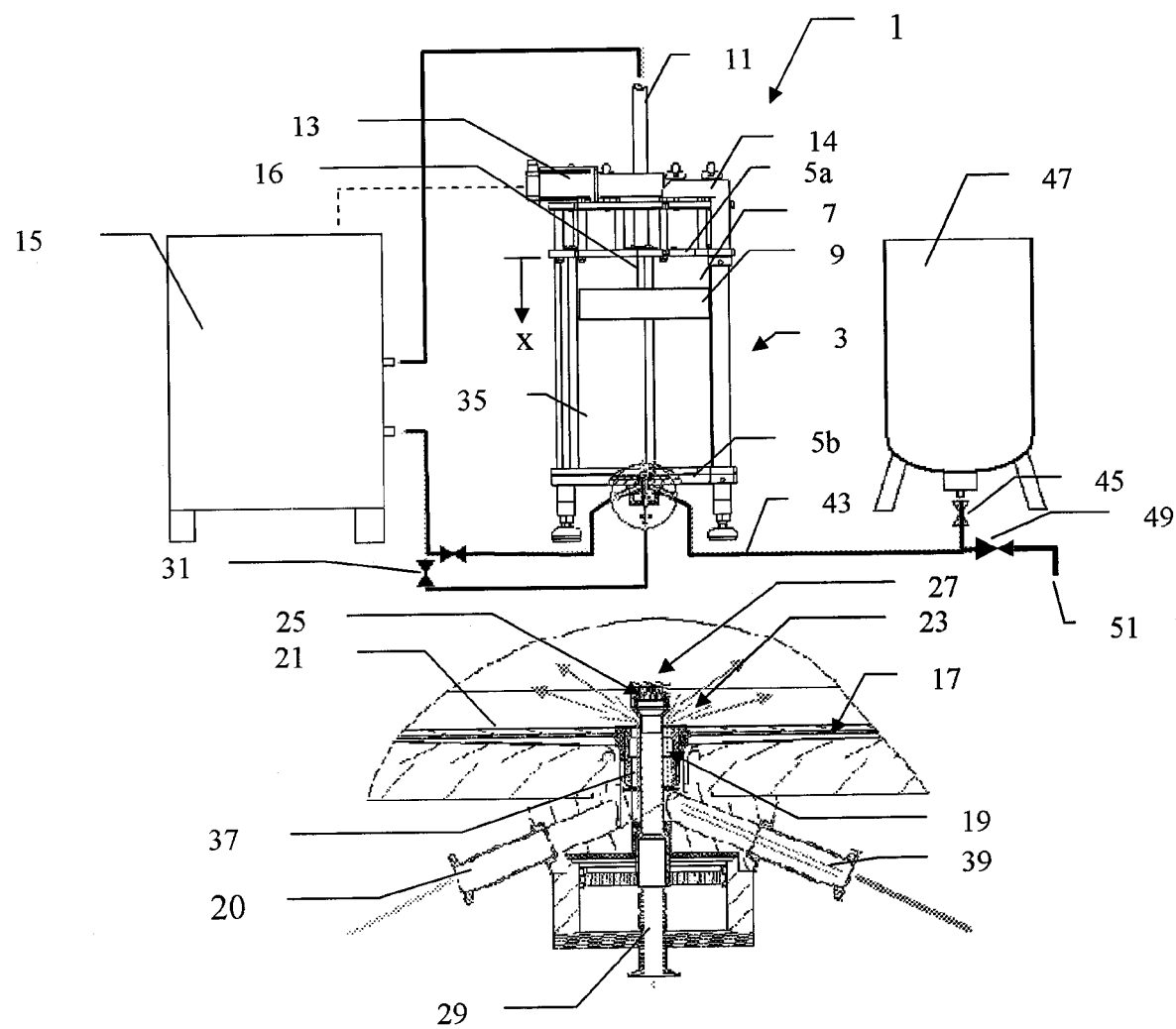
FIG. 1 shows a schematic side view of a media packing system in accordance with the present invention.

FIG. 1 shows schematically an automated column packing system 1 in accordance with one embodiment of the present invention in which components unrelated to the present invention are omitted for ease of illustration of the principles of the present invention. System 1 comprises a column 3 which comprises upper lid or flange 5a and lower end plate 5b surrounded by a cylindrical column wall 7. Positioned between the lid or flange 5a and lower endplate 5b in column 3 is a movable adapter 9 (which may be provided with a sample distribution system, not shown, intended to distribute incoming liquid substantially evenly over the cross-section of the column 3, and a bed support, not shown, extending over the cross-section of the column with a mesh fine enough to prevent bed particles from passing through it) connected to a column inlet 11 connectable to supplies of liquids (not shown) such as sample mixtures, eluants, buffers, etc. Movable adapter 9 is movable in the longitudinal direction of the column by an actuator 13, such as a motor or piston/cylinder actuator, supported on a frame 14 passing over the upper end of the column wall 5. Movable adapter position sensing means 16 are provided to determine the position ("x") of the movable adapter relative to a fixed level, for example the upper side of the lower endplate 5b, and a signal corresponding to this distance x is sent to a control unit 15. The operation of actuator 13 and the corresponding up or downwards movement of movable adapter 9 is controllable by the automated control unit 15. Control unit 15 preferably comprises hardware and software for controlling the operation of the column 3. Control unit controls the opening and closing of valves, the speed of movable adapter movement and the amount of movable adapter movement. Control unit 15 is also provided with means for measuring the force required to move the movable adapter 9—either directly, for example by measuring motor torque or actuator working pressure, or indirectly, for example by measuring column interior pressure or strain in the container wall, frame, lid, movable adapter or endplate.

Lower end plate 5b supports a fluid collection system 17 leading to an annular duct 19. The collection system 17 is positioned between a bed support 21 and the annular duct 19, and is intended to collect fluid evenly over the cross-section of the column and deliver it to annular duct 19. Annular duct 19 is connected to a mobile phase outlet 20 which transports the mobile phase away from the column for further processing. The bed support 21 is intended to support the weight of the bed in the column and to prevent bed media form leaving the column. The bed support 21 may, for example, be a mesh or net with apertures small enough to prevent bed media passing through the bed support. Lower endplate 5b further comprises a central aperture 23 into which a movable nozzle arrangement 25 is mountable. The nozzle arrangement comprises a cleaning-in-place (CIP) nozzle 27 connected via pipeline 29 and a remotely controllable valve 31 to for recirculating cleaning fluid in the system. Recirculation valve 31 is controllable by control unit 15. Nozzle 27 is extendable from a closed position in which it is in a leak-tight engagement with the bed support 21 and blocks central aperture 23, to an open position in which it projects through the bed support 21 into the cavity 35 of the column formed between bed support 21 and movable adapter 9. Central aperture 23 is surrounded by an annular duct 19 which is connected to a media duct 39 which is connectable to a pipeline 43 which is connectable via slurry tank valve 45 to slurry tank 47 and via drain valve 49 to a drain 51. Annular duct 19 is in fluid communication with column cavity 35 when nozzle 27 is in the open position and is blocked from fluid communication with the cavity 35 when nozzle 27 is retracted to the closed position.

In order to pack the column with bed media, the control unit is programmed with relevant media information such as the desired packed bed height (which may differ to the actual packed bed height achieved) and assumed slurry concentration, or volume of the slurry (which has a specified particle concentration which is assumed to be achieved in practice) to be fed into the column and the adapter descent speed necessary to give the required settled bed height, and the required amount of compression of the bed—the "compression factor"—needed to give the optimum performance. The amount of bed compression required may be given as a percentage of the settled bed height, for example if the amount of slurry fed into a column is sufficient to give a settled bed height of 1 m at a adapter descent speed of 1 cm/min and the amount of compression required is 15% then the target bed height will be 85 cm. Typically the amount of compression required can be between 1% and 50% and is dependant, amongst others, on the column size, type and particle size of the bed media and the settled bed height. The predetermined volume of slurry containing bed media particles is introduced into the column, for example by suction by raising movable adapter 9 under the control of control unit 15 with slurry tank valve 45 open, nozzle 27 in the projecting open position and recirculation valve 31 closed—this causes slurry to be sucked from slurry tank 47 through slurry valve 45 along pipeline 43 through port 39 and though annular duct 19 into cavity 35. Movable adapter 9 is stopped by control unit 15 when it reaches the distance x necessary to suck the required volume of slurry into the column.

In packing mode the media valve media opening 37 is closed by retracting nozzle 27 and closing slurry tank valve 45. Mobile phase outlet 20 is opened to allow excess fluid to leave the column. Movable adapter 9 is moved down at a constant speed (e.g. between 0.5 and 10 cm per minute) and as it descends it meets the settled bed and starts to compress it axially—this position is called the "breakpoint". Compression of a bed of particles in a column with a movable adapter can be can be defined as starting at the position of the movable adapter at which there is first an unbroken path of particles over substantially the whole of the cross-sectional area of the column between the adapter and the end of the column that it is moving towards. In the case of a system in which the descent of the adapter towards the end of the column at a constant speed has been characterised by a substantially constant force required to move the adapter, this position is shown by an increase in the force required to move the adapter. In the case of a system in which the descent of the adapter towards the end of the column at a constant speed has been characterised by a continuously increasing force required to move the adapter, this position is shown by an increase in the rate of increase in the force required to move the adapter. Thus, at the breakpoint the force required to move the movable adapter 9 at the constant speed increases due to the increasing resistance to adapter movement caused by the bed particles being forced closer together as opposed to merely displacing liquid in order to fill voids in the bed. Movable adapter 9 is moved down the distance necessary to compress the bed until the desired bed compression is reached.

Figure 2:
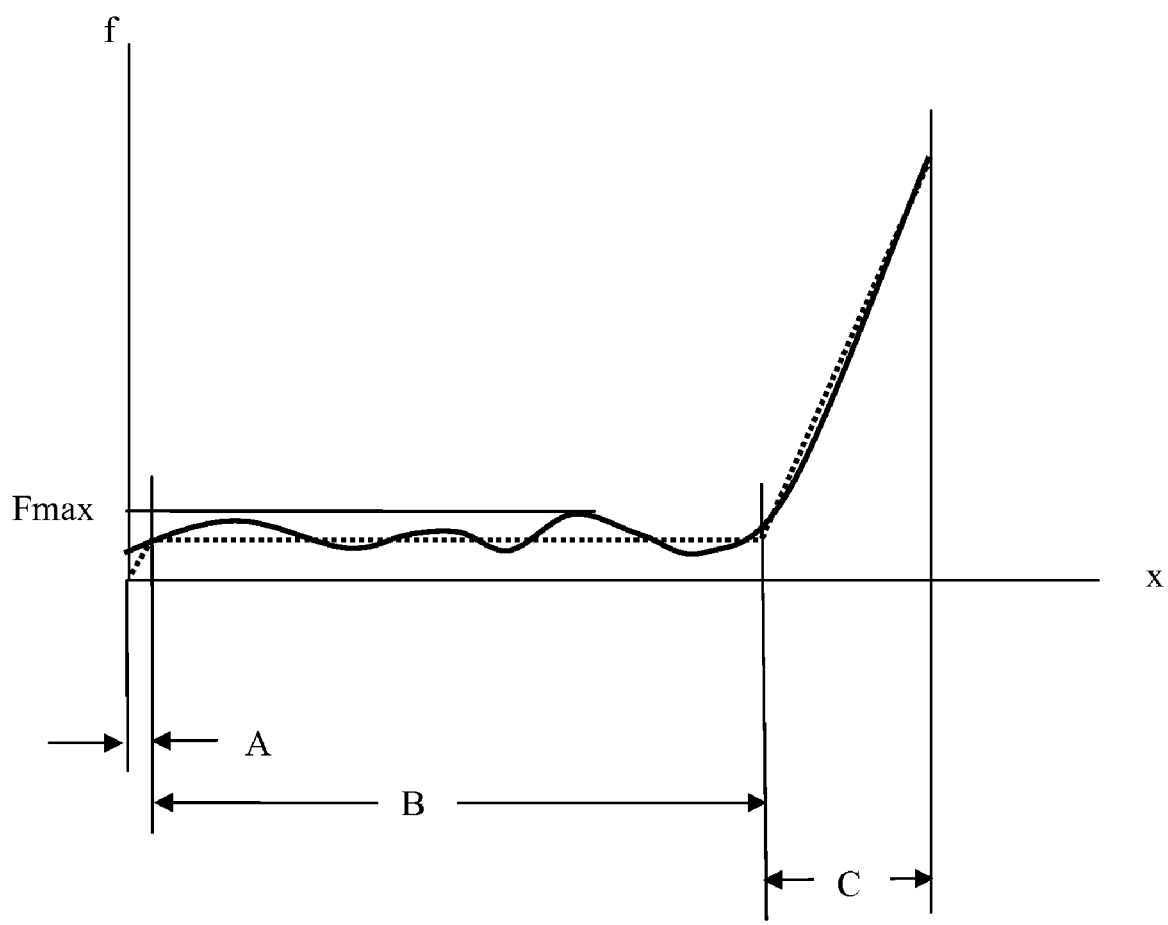
FIG. 2 shows an example of the typical shape of a plot of force required to move a movable adapter against distance during packing of a settled bed of media.

In order to obtain the correct amount of bed compression it is necessary to determine the breakpoint. In manually operated systems this is determined by the operator. An automated system must have an automated means for determining the breakpoint. This is not easy as owning to factors such as varying friction between the column wall and the moving adapter, inhomogenuities in the settled bed, measurement errors, etc a real life plot of adapter position x against force f does not follow the theoretical curve. This is illustrated in FIG. 2. The dotted line shows a theoretical plot of how actuator force should vary against movable adapter position as the adapter moves down a column. The first portion A of the theoretical plot shows a rise in force as the adapter starts to move and force liquid out of the column. Portion B shows a flat curve which represents the adapter pressing liquid out of the column while descending at a constant speed. This settles the bed. Portion C shows a substantially steady increase in the force as the media in the bed is packed together and compressed. The intersection of portions B and C is the breakpoint which represents the start of settled bed compression. The position of the adapter at this point corresponds to the settled bed height. This height is used as the start point for calculating how much further the adapter needs to move in order to achieve the optimally compressed packed bed height. The position of the adapter at the other end of portion C corresponds to the optimally compressed packed bed.

The solid line in FIG. 2 shows a representation of a practical plot of how actuator force varies against movable adapter position as the adapter moves down a column. In portion B the force varies up and down and the transition between portion B and portion C is not indicated by a sharp breakpoint but by a curve. This makes it difficult to determine exactly where bed compression starts.

In order to do this, the control unit 15 is provided with software which can run a bed compression algorithm which calculates when the bed compression by the adapter coming into contact with the settled bed starts (i.e. determines the breakpoint) and when bed compression should end (i.e. when the bed has been compressed the required amount from the breakpoint).

In one embodiment of the present invention, the algorithm may take an average of the signal s corresponding to the force needed to move the movable adapter recorded during part or all of the time that the movable adapter is moving without being in contact with the bed (i.e. the portion B of the curve of force against position) and an average of the slope of the curve recorded during a portion of the time that the bed is being compressed (i.e. the portion C of the curve of force against position), and calculate the intersection of these two portions. This requires the software to be able to determine if a signal value is in portion B or portion c of the curve. One way of doing this is to estimate a position X1 which is the estimate height of the settled bed and calculate the average force Fav during the travel of the movable adapter over a proportion of its movement from its starting position (when X=0) to the position X1. For example the average could cover the period from X=0.1×X1 to X=0.9×X1, or from X=0.2×X1 to X=0.75×X1, etc. The maximum force Fmax recorded in this region could also be stored. Once the movable adapter has reached the settled bed the force required to move the adapter will start to rise. The software could be programmed to start calculating the slope of the force against distance curve once the force reaches a multiple (e.g 2 times, 2.5 times, 3 times, etc) of the maximum force Fmax recorded earlier. This can be done by comparing the actual force and position against one or more previous force and position readings. The calculated slope is then used to calculate a calculated intersection with a line corresponding to the average force Fav. The distance Xcal at this intersection is then assumed to be the position where the movable adapter came into contact with the settled bed and started to compress it—the calculated breakpoint. This can be repeated and an average value of the calculated breakpoint position Xcal calculated. As the movable adapter moves its position from Xcal is calculated and when it exceeds a distance corresponding to a bed compression of, for example 75% of the desired bed compression based on the current Xcal, the last current value Xcal is assumed to be the true height of the settled bed, the required end position of the movable adapter needed to give the required bed compression is calculated and the movement of the movable adapter is continued until it reaches the required end position.

In alternative embodiment of the present invention, the movable adapter is not moved by a motor but by pumping liquid, such as water, in or out of the sealed space between the adaptor and the lid 5a. The bed compression algorithm monitors the pressure in this space. The pressure in this space starts to rise (or, if the monitored pressure was showing a substantially constant rate of increase, the rate of increase starts to increase) when the adaptor reaches the bed and the algorithm calculates the position where the pressure rise starts. The pressure signal is very noisy and the rise may be non-linear—in which case, the use of filter specified below removes the noise and makes the rise substantially linear.

The start of the pressure rise is calculated by observing the filtered pressure signal (dp) and capturing it and the current position (x) when the in-signal rises above specified levels. There are two such levels—dp1 and dp2—where dp2 is greater than dp1. When level dp2 is reached the parameters for a straight line through the captured points (x1,dp1) (x2, dp2) are calculated. This line is supposed to approximate to the rising slope of the signal. The point where this line cross the x-axis is then assumed to be the position where the compression of the bed starts and is called the breakpoint. This point can then be used to determine the further column movement required to give the desired bed compression.

Filter Design

The filter converts the pressure signal to a signal that is flat and near zero except when the in-signal is raised: then the signal also is raised.

The current implementation is an IIR-filter followed by a difference:

$$y(n)=a*y(n-1)+b*y(n-2)+c*x(n)$$

$$s(n)=y(n)-y(n-1) \quad (1)$$

By tests using actual data the following parameters have been selected:

$$a=1.9495, b=-0.95, c=0.005$$

The reasoning behind this filter is this:

Imagine a mechanical system with a mass m connected to a spring and all inside a viscous medium. Attach the in-signal as the position of the loose spring-end and you will have:

my"+ry'+k(y-x)=0 (y=position of the mass. x=position of the other spring end, r=viscosity, k=spring coefficient)

This can be rewritten as: $y''+(r/m)y'+(k/m)y=(k/m)x$ or $y''+Ay'+By=Cx$.

Approximating derivatives with differences:

$$y'(n-1)=(y(n-1)-y(n))/h \quad (2)$$

$$y''(n-1)=(y(n)+2y(n-1)+y(n-2))/h^2 \quad (3)$$

For stability reasons we select the (n−1) sample for y and x. This results in:

$$y_{n-2}-2y_{n-1}+y_{n-2}+(hr/m)(y_{n-1}-y_{n-2})+(h^2 k/m)(y_{n-1}-x_{n-1})=0 \quad (4)$$

rearrange:

$$y_{n-2}+((h^2 k/m)+(hr/m)-2)y_{n-1}+(1-(hr/m))y_{n-2}=(h^2 k/m)x_{n-1} \quad (5)$$

or $$y_{n-2}=(2-(h^2 k/m)-(hr/m))y_{n-1}+((hr/m)-1)y_{n-2}+(h^2 k/m)x_{n-1} \quad (6)$$

with $a=(2-(h^2 k/m)-(hr/m))$, $b=((hr/m)-1)$, $c=(h^2 k/m)$ we get (1)

Experiments with m,r,k will give us the best values. This is easy since m can be interpreted as "heaviness", r as "greasyness" and k as "springyness".

The difference is added to remove low frequency components and to linearize the rising pressure.

While the invention has been illustrated by examples of embodiments in which slurry is sucked into columns by moving the movable adapter, it is also conceivable to directly pump slurry into columns. Additionally it is also conceivable to move the adapter at non-constant speeds during settling of the bed and compression of the settled bed, for example starting bed settling at an adapter speed of e.g. 10 cm/min and lowering the adapter speed as the adapter approaches the estimated settled bed height and then continuing lowering the adapter at a slower speed e.g. 0.5 cm/min. These adapter speeds are only mentioned as illustrative examples and any suitable adapter speed may be used, for example from less than 0.5 cm/min e.g. 0.1 cm/min to more than 10 cm/min, e.g. 12.5 cm/min.

It is furthermore conceivable that a packing system in accordance with the present invention is provided with manual controls so that an operator is permitted to control the adapter speed during some or all of the packing procedure and the software is used to monitor the movement of the adapter and to calculate the breakpoint. The position of the calculated breakpoint, optionally with information on the calculated position of the adapter needed to achieve the desired compression factor, can be provided to the operator who then controls the movement of the adapter until it reaches the position corresponding to the desired bed compression.

The invention has been illustrated by examples of embodiments in which the column is cylindrical and has a constant diameter, thereby enabling a linear correlation between cylinder volume and bed height, it is also conceivable to adapt the present invention for application to other column shapes in which the correlation is non-linear.

Those skilled in the art, having the benefit of the teachings of the present invention as set forth above, can effect numerous modifications thereto. These modifications are to be construed as being encompassed within the scope of the present invention as set forth in the appended claims.

What is claimed is:

1. A column packing system comprising an automated control unit including automation software and hardware and a column having a longitudinal axis and a movable adapter, movable by pumping liquid in or out of a sealed space between said movable adapter and a lid of said column, said movable adapter being movable by pumping liquid in or out of a sealed space between said movable adapter and a lid of said column, while being monitored by the control unit, wherein the control unit is configured to pack the column with a settled bed of media based on the control unit having relevant media information of a desired packed bed height, a volume of slurry with a specified particle concentration and a descent speed the movable adapter has to move to provide a required settled bed height and a required amount of compression of the settled bed of media, wherein said automation software of the control unit is adapted to determine a breakpoint when said movable adapter begins to compress said settled bed of media by calculating the position where a pressure rise starts in said sealed space and also adapted to calculate the distance that said movable adapter has to move from said breakpoint to achieve a predetermined amount of bed compression and to control the movement of said movable adapter to the position corresponding to the distance.

2. The column packing system of claim 1, wherein said software is able to produce an operator readable signal corresponding to the position of the breakpoint.

3. The column packing system of claim 2, wherein said software is able to calculate the distance that said movable adapter has to move from said breakpoint to achieve the predetermined amount of bed compression and is able to produce an operator readable signal corresponding to that distance.

4. The column packing system of claim 1, wherein the column is a chromatography column and the bed includes a chromatography medium.

* * * * *